United States Patent [19]

Crawford

[11] 4,101,428
[45] Jul. 18, 1978

[54] COMPOSITION COMPRISING A MIXTURE OF THE ZINC SALTS OF O,O-DI(PRIMARY AND SECONDARY) ALKYLDITHIOPHOSPHORIC ACIDS

[75] Inventor: John Crawford, Hornsea, England

[73] Assignee: Chevron Research Company, San Francisco, Calif.

[21] Appl. No.: 770,866

[22] Filed: Feb. 22, 1977

[30] Foreign Application Priority Data

Feb. 25, 1976 [GB] United Kingdom ............... 7402/76

[51] Int. Cl.$^2$ .................. C10M 1/48; C10M 3/42; C10M 5/24; C10M 7/46
[52] U.S. Cl. .......................... 252/32.7 E; 252/400 A
[58] Field of Search ................... 252/32.7 E, 400 A

[56] References Cited

U.S. PATENT DOCUMENTS

| | | | |
|---|---|---|---|
| 2,680,123 | 6/1954 | Mulvany | 252/32.7 E |
| 3,318,808 | 5/1967 | Plemich et al. | 252/32.7 E |
| 3,385,791 | 5/1968 | Colyer et al. | 252/32.7 E |
| 3,523,082 | 8/1970 | Vienna et al. | 252/32.7 E |
| 3,923,669 | 12/1975 | Newingham et al. | 252/32.7 E |

*Primary Examiner*—Delbert E. Gantz
*Assistant Examiner*—Irving Vaughn
*Attorney, Agent, or Firm*—D. A. Newell; C. J. Tonkin; J. J. DeYoung

[57] ABSTRACT

A mixture of the zinc salts of O,O-dialkyldithiophosphoric acids prepared by contacting a feedstock comprising a mixture of one or more $C_1$ to $C_{30}$ primary alcohol(s) and one or more $C_4$ to $C_{20}$ secondary alcohol(s) with $P_2S_5$ to form a mixture of O,O'-dialkyldithiophosphoric acids and thereafter neutralizing the mixture of acids by contact with zinc oxide, the secondary alcohol(s) forming not less than 25 mol.% of the feedstock mixture.

8 Claims, No Drawings

COMPOSITION COMPRISING A MIXTURE OF THE ZINC SALTS OF O,O-DI(PRIMARY AND SECONDARY) ALKYLDITHIOPHOSPHORIC ACIDS

The present invention relates to zinc salts of O,O'-dialkyl dithiophosphoric acids and to their use as lubricant additives.

In the past many dithiophosphate compounds have been employed as additives in lubricant compositions primarily to reduce wear and to act as antioxidants. Of the many compounds employed perhaps the best known are the zinc salts of O,O'-dihydrocarbyl dithiophosphoric acids. Normally the zinc salts are prepared by reacting phosphorus pentasulphide with an alcohol to form the corresponding dithiophosphoric acid and thereafter neutralising the acid with zinc oxide.

In practice it is found that the zinc salts of acids derived from secondary alcohols are more effective wear inhibitors than the zinc salts of acids derived from primary alcohols. On the other hand the thermal stability of zinc dialkyldithiophosphates derived from secondary alcohols is lower than those derived from primary alcohols. A blend of the two types of zinc dialkyldithiophosphates results in a balance of anti-wear effectiveness and thermal stability dependent on the relative proportions of the two types in the blend.

It has now been found that zinc dialkyldithiophosphates prepared from a mixture of primary and secondary alcohols exhibit a higher thermal stability without any substantial adverse effect on their anti-wear properties than do the corresponding blends.

Thus according to the present invention there is provided a mixture of the zinc salts of O,O'-dialkyldithiophosphoric acids having the structural formula:

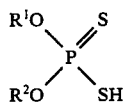
(A)

wherein $R^1$ and $R^2$ are the same or different and are either $C_1$ to $C_{30}$ primary alkyl groups or $C_4$ to $C_{20}$ secondary alkyl groups, which mixture is prepared by contacting a feedstock comprising a mixture of one or more $C_1$ to $C_{30}$ primary alcohol(s) and one or more $C_4$ to $C_{20}$ secondary alcohol(s) with phosphorus pentasulphide to form a mixture of O,O'-dialkyldithiophosphoric acids of structure (A), and thereafter neutralising the mixture of acids by contact with up to 60% molar excess of an alkaline zinc compound, the secondary alcohol(s) forming not less than 25 mole percent of the feedstock mixture.

Preferably the primary alcohol is a $C_4$ to $C_{18}$, even more preferably a $C_6$ to $C_{12}$, primary alcohol.

Preferably the secondary alcohol is a $C_4$ to $C_{12}$, even more preferably a $C_4$ to $C_{10}$, secondary alcohol.

Preferably the alkaline inorganic zinc compound is zinc oxide.

The amount of alkaline inorganic zinc compound used to neutralise the mixture of dialkyldithiophosphoric acids is preferably from 10 to 30% molar, even more preferably from 15 to 25% molar, in excess of the stoichiometric quantity required to completely neutralise the acids. The reaction is believed to proceed according to the following equations:

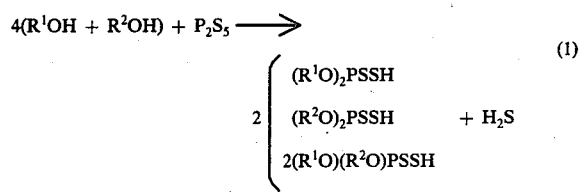

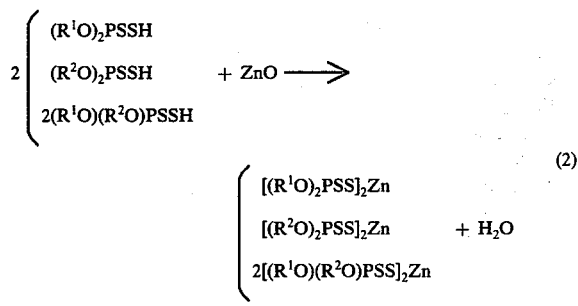

In addition to the neutral zinc salts formed according to equations (1) and (2) varying amounts of basic zinc salts may also be formed in the following reaction:

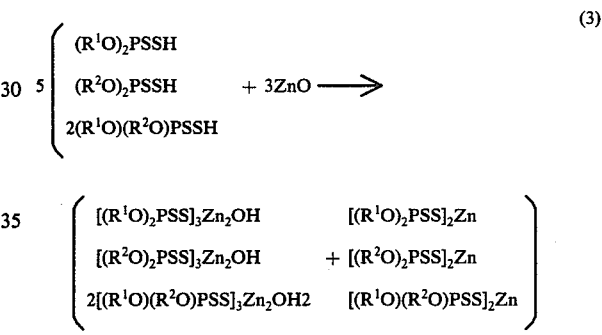

Preferably the secondary alcohol(s) form not less than 30 and not more than 70, even more preferably not less than 40 and not more than 60, mole percent of the feedstock mixture.

The reaction conditions are well known in the art. Typically one mole of phosphorus pentasulphide may be reacted with about 4 moles of the mixture of alcohols at a temperature sufficient to cause reaction, e.g. 40° to 100° C and held at this temperature until evolution of $H_2S$ ceases, preferably whilst purging with an inert gas e.g. nitrogen. The mixture may then be cooled and, optionally, unreacted phosphorus pentasulphide filtered off. The mixed dialkyldithiophosphoric acids may then be admixed with a suitable solvent, such as n-heptane, benzene or toluene and contacted with zinc oxide. Alternatively the mixed acids may, preferably, be contacted with a slurry of zinc oxide and solvent neutral base oil. Up to 20% by weight solvent neutral base oil may be used in the slurry but it is preferred to employ from 10 to 12% by weight. Water formed during the neutralisation may, preferably, be removed under vacuum at elevated temperature during the reaction or from the final product. Finally the mixture may be filtered to remove any solids therefrom.

The mixture of the zinc salts of O,O'-dialkyldithiophosphoric acids dissolved in solvent neutral base oil, as prepared, conveniently forms a concentrate which may be blended with oils of lubricating viscosity to form a finished lubricant composition. Other additives conventionally incorporated into finished lubricant compositions may be blended into the concentrate or incorporated directly into the finished lubricant composition.

Thus according to another aspect of the present invention there is provided a finished lubricant composition comprising a major amount of a lubricating base oil and a minor amount of a mixture of the zinc salts of 0,0′-dialkyl dithiophosphoric acids as hereinbefore described.

The finished lubricant composition may suitably contain from 0.001 to 15% by weight, preferably from 0.01 to 5% by weight of the mixture of the zinc salts of 0,0′-dialkyldithiophosphoric acids.

In addition to the mixture of zinc salts of 0,0′-dialkyldithiophosphoric acids the composition may contain other additives commonly used in lubricating oils, such as dispersants, antioxidants, pour-point depressants, corrosion inhibitors and the like.

The following Examples further illustrate the invention:

EXAMPLE 1

222g (1 mole) of phosphorus pentasulphide was added to a mixture of primary and secondary alcohols made up as follows:

286g (2.2) moles of a $C_8$ primary alcohol (alphanol)
112.2g (1.1) moles of methyl isobutyl carbinol (secondary alcohol)
81.4g (1.1) moles of sec-butanol (secondary alcohol)

The temperature of the mixture was increased gradually to 80° C over a period of 2 hours. The mixture was heated for a further 6 hours to facilitate the removal of hydrogen sulphide, aided by the introduction of a nitrogen purge.

The resulting liquid was allowed to cool and then poured on to a slurry of 100g of zinc oxide and 100g of 100 solvent neutral oil. Vacuum was applied and the temperature raised to 100° C, water of reaction being removed in the conventional manner by a condenser receiver system. After 2 hours the mixture was filtered to give 699g of a mixture of zinc salts of dialkyldithiophosphoric acids dissolved in solvent neutral base oil.

The product mixture was analysed for phosphorus, zinc and sulphur. The results of the analysis are given in Table 1.

EXAMPLE 2

22g (1mole) of phosphorus pentasulphide was added to a mixture of:

286g (2.2 moles) of a primary $C_8$ alcohol (alphanol) and
162.8g (2.2 moles) of sec-butanol Thereafter the same procedure was followed as that described in Example 1. The results of the analysis of the product are given in Table 1.

Table 1

| | Chemical Analysis of Products | | | |
|---|---|---|---|---|
| Analysis | | | Commercial Products | |
| | Example 1 | Example 2 | X | Y |
| P | 7.33% | 7.63% | 7.0–7.8% | 6.8–7.6% |
| Zn | 8.06% | 8.60% | | |
| | (110% P) | (112.7% P) | 105–115% P | 7.14–8.74% |
| S | 13.61% | 14.37% | | |
| | (186% P) | (188.3% P) | 190% P min′″ | 190% P min′″ |

X is a commercial product consisting of the zinc dialkyldithiophosphate manufactured from the primary $C_8$ alcohol, alphanol.

Y is a commercial product consisting of the zinc dialkyldithiophosphate manufactured from a mixture of 70% wt. sec-butanol and 30% wt. methyl isobutyl carbinol.

EXAMPLE 3

The products obtained in Examples 1 and 2 and the commercial products were evaluated in a 'cloud point' test in which a 5% w/w solution of the additive in white oil (liquid paraffin) is heated at a constant rate (5° C/min.) in a test tube. The cloud point is the temperature at which decomposition occurs and is identified by the mixture turning white. The observed values of the cloud point are given in the following Table 2.

Table 2

| Cloud-Points of Products | |
|---|---|
| Product | Cloud Point ° C |
| X | 240 |
| *Z | 227 |
| Y | 208 |
| Example 1 | 232 |
| Example 2 | 229 |
| 50/50 X/Y | 212 |

*Z is a commercial zinc dialkyl dithiophosphate manufactured from 1.5 mole iso-butanol and 1 mole n-hexanol.

Examination of Table 2 shows that the product prepared from a secondary alcohol (Y) has the lowest thermal stability. The product prepared from a $C_8$ primary alcohol (X) has the highest thermal stability. A 50:50 mixture of the most stable and the least stable has a thermal stability very much closer to the least stable. However the products of Examples 1 and 2 have thermal stabilities comparable or better than Z and approaching X in the case of the product of Example 1.

EXAMPLE 4

The products of Examples 1 and 2 and the commercial products were evaluated in a Petter W1 single cylinder petrol engine run to Def 2101D but extended beyond the normal 36 hours. The results of these engine tests are given in Table 3.

Table 3

| | Engine Test Results | | | | |
|---|---|---|---|---|---|
| Material | Y | Z | 50/50X/Y blend | Example 1 | Example 2 |
| Bearing Wt. loss | | | | | |
| 36 hours | 9 | 54 | 4 | 11 | 9 |
| 48 hours | 20 | 66 | 10 | 12 | 15 |
| 60 hours | 22 | 70 | 22 | 15 | 17 |
| % Viscosity increase | | | | | |
| 36 hours | — | 20 | 34.7 | 28 | 23 |
| 48 hours | 44 | 45 | 51.3 | 35 | 43 |
| 60 hours | 53 | — | 62.4 | 46 | 46 |

Table 3-continued

| | Engine Test Results | | | | |
|---|---|---|---|---|---|
| Material | Y | Z | 50/50X/Y blend | Example 1 | Example 2 |
| Undercrown (10 clean) | 9.6 | 9.8 | 8.2 | 9.9 | 9.6 |

The results confirm that the anti-wear properties compare very well with zinc dialkyldithiophosphates prepared exclusively from primary or secondary alcohols and compare reasonably well with the blend.

EXAMPLE 5

The anti-wear properties were tested using the Shell four-ball machine. The test involved pressing a rotating steel ball against a triangle of three stationary steel balls lubricated with the test oil.

Two tests were used:

THE WELD POINT TEST

The pressure on the rotating ball was increased until all four balls welded together. Thirty second tests were run at 10 kg intervals until welding occurred. This weight is known as the weld point.

THE ANTI-WEAR TEST

The load on the rotating ball was kept constant at 15 kg and the test was run for 1 hour. After this period the scars on the three stationary balls were measured using a vernier microscope.

The anti-wear properties for the products and comparison compounds are given in Table 4.

Table 4

| | Anti-wear Properties | |
|---|---|---|
| Product | Weld Point (kg) | Anti-wear Scar (mm) |
| X | 200 | 0.276 |
| Y | 230 | 0.277 |
| Example 1 | 220 | 0.279 |
| Example 2 | 220 | 0.277 |

In the Weld Point Test the product of the invention provided a higher Weld Point than the commercial product produced exclusively from a primary alcohol (X) and almost as high as the commercial product produced exclusively from a secondary alcohol (Y). The Anti-wear Scar did not discriminate sufficiently between the products to draw any meaningful conclusions other than that the products of the invention were comparable with the commercially available products.

I claim:

1. A lubricant composition comprising a major amount of a lubricating base oil and from 0.001 to 15% by weight of a mixture of zinc salts of 0,0'-dialkyldithiophosphoric acids having the structural formula:

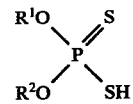

wherein $R^1$ and $R^2$ are the same or different and are either $C_1$ to $C_{30}$ primary alkyl groups or $C_4$ to $C_{20}$ secondary alkyl groups, and wherein said mixture is prepared by contacting a feedstock comprising a mixture of one or more $C_1$ to $C_{30}$ primary alcohol(s) and one or more $C_4$ to $C_{20}$ secondary alcohol(s) with phosphorus pentasulphide to form a mixture of 0,0'-dialkyldithiophosphoric acids and thereafter neutralising the mixture of acids by contact with zinc oxide, the secondary alcohol(s) forming not less than 25 mole percent of the feedstock mixture.

2. A composition according to claim 1 wherein the primary alcohol is a $C_4$ to $C_{18}$ primary alcohol and the secondary alcohol is a $C_4$ to $C_{12}$ alcohol.

3. A composition according to claim 2 wherein the primary alcohol is a $C_6$ to $C_{12}$ primary alcohol and the secondary alcohol is a $C_4$ to $C_{10}$ secondary alcohol.

4. A composition according to claim 1 wherein the amount of alkaline inorganic zinc compound used to neutralize the mixture of dialkyldithiophosphoric acids is from 10 to 30% molar in excess of the stoichiometric quantity required to completely neutralize the acids.

5. The composition according to claim 4 wherein the amount of alkaline inorganic zinc compound is from 15 to 25% molar in excess of the stoichiometric quantity required to completely neutralize the acids.

6. A composition according to claim 1 wherein the secondary alcohols form not less than 30 and not more than 70 mol percent of the feedstock mixture.

7. A composition according to claim 1 wherein the secondary alcohols form not less than 40 and not more than 60 mol percent of the feedstock mixture.

8. The composition of claim 1 wherein said primary alcohol is a $C_8$ primary alcohol and said secondary alcohol is sec-butanol, methyl isobutyl carbinol or a mixture thereof.

* * * * *